United States Patent
Wayman et al.

(10) Patent No.: US 6,967,478 B2
(45) Date of Patent: Nov. 22, 2005

(54) PIPE CONDITION DETECTING APPARATUS

(75) Inventors: Malcolm Wayman, Newcastle upon Tyne (GB); Dudley Dickson, Newcastle upon Tyne (GB)

(73) Assignee: Advanced Engineering Solutions, Ltd., Cramlington (GB)

( * ) Notice: Subject to any disclaimer, the term of this patent is extended or adjusted under 35 U.S.C. 154(b) by 8 days.

(21) Appl. No.: 10/157,345

(22) Filed: May 29, 2002

(65) Prior Publication Data

US 2003/0011363 A1 Jan. 16, 2003

(30) Foreign Application Priority Data

May 30, 2001 (GB) .................................. 0112983

(51) Int. Cl.[7] ............................................. G01N 27/82
(52) U.S. Cl. ....................... 324/238; 324/235; 324/240
(58) Field of Search ............................... 324/219, 220, 324/221, 238, 239, 240, 241, 242, 243, 235

(56) References Cited

U.S. PATENT DOCUMENTS

| | | | |
|---|---|---|---|
| 3,694,740 A | * 9/1972 | Bergstrand ................. 324/227 |
| RE29,166 E | * 3/1977 | Forster ....................... 324/205 |
| 4,303,883 A | * 12/1981 | Mori et al. ............ 324/207.18 |
| 4,611,170 A | * 9/1986 | Stanley et al. ............... 324/239 |
| 4,789,827 A | * 12/1988 | Bergander .................. 324/220 |
| 4,814,705 A | * 3/1989 | Saunderson ................ 324/225 |
| 5,293,117 A | * 3/1994 | Hwang ........................ 324/220 |
| 5,532,587 A | * 7/1996 | Downs et al. ............... 324/220 |
| 5,581,037 A | * 12/1996 | Kwun et al. .................. 73/623 |
| 5,793,205 A | * 8/1998 | Griffith et al. .............. 324/238 |
| 5,864,232 A | * 1/1999 | Laursen ...................... 324/220 |
| 6,037,767 A | * 3/2000 | Crescenzo et al. .......... 324/220 |
| 6,150,809 A | * 11/2000 | Tiernan et al. ............. 324/238 |

* cited by examiner

Primary Examiner—Jay Patidar
(74) Attorney, Agent, or Firm—Woodard, Emhardt, Moriarty, McNett & Henry LLP

(57) ABSTRACT

The invention relates to apparatus and a method for detecting the condition of the material of a pipeline wall. The apparatus includes means for inducing and detecting magnetic flux at a location on the pipeline and, at said location, sensing means detect whether any change in material condition is on or near the external wall of the pipeline. By analysing the two sets of monitored values a change in condition, such as corrosion, can be detected, located and determined to be at or near the external or internal surfaces of the pipeline wall.

13 Claims, 13 Drawing Sheets

PIPE CONDITION DETECTING APPARATUS

The invention to which this application relates is the provision of apparatus and a method for detecting the condition of a pipe.

It is known to provide apparatus which can be used to assess the quality, damage, and/or risk of failure of pipelines which have been in service for a period of time and, from the information provided by the apparatus and method, to then assess whether the pipe is in a dangerous condition, needs specific maintenance and so on. This therefore avoids the need for the pipeline to be completely replaced and/or ensures that if the pipeline is in a dangerous state of decay, it can be relatively easily identified without the need to excavate the entire pipe and replace same.

A common, known, process, is to send an item of apparatus, typically known in the trade as a "PIG", along the interior of the pipeline with the same being carried by the flow of the gas or liquid as it flows along the pipeline interior. As it passes along the interior of the pipe, results from a series of sensors and/or other detection apparatus mounted on the PIG forms a survey of the pipeline interior and exterior condition. However, a problem is that this type of apparatus is not always suitable or compatible with particular liquids or gases which pass along the pipeline interior. For example, there is a general resistance to allow "pigs" and other forms of apparatus to pass along the interior of a pipeline which carries water for fear of causing contamination to the water. Thus, the use of pigs is generally regarded as being impractical or potentially dangerous to the quality of some liquids passing along the pipeline.

It is also known to provide apparatus which can travel along the exterior surface of a pipeline. This form of apparatus can be provided with means to allow the same to be moved along the exterior of the pipeline. In one embodiment a magnetic flux is generated which passes into the pipeline. As the apparatus moves along the pipeline, the level of the magnetic flux level is monitored to ensure that any changes in flux ate detected. This change can be caused by "leakage" and is indicative of reduced pipe wall thicknesses. As a result the possible corrosion or damage to the pipe wall is indicated and mapped with respect to the position of the apparatus on the pipeline.

With many types of pipeline, this form of apparatus can be satisfactory in that the magnetic flux indicates the position of a defect and a subsequent inspection of the external surface of the pipeline indicates to the user whether the defect is on the external surface of the pipeline. If it is visible then magnetic flux can be used to determine the depth of the fault but if not visible, the fault is then assumed to be on the interior wall of the pipeline and the magnetic flux change can again be used to determine the size and depth of the fault. This apparatus is therefore available for use where a visual check of the external pipeline can be used to determine the position of the defect indicated by a magnetic flux change.

However, with certain materials, such as for example cast iron, there may be defects on the exterior of the pipe which are not visible and therefore the apparatus which is available at the present cannot be used as a visual check of the external surface is not guaranteed to identify whether or not an external or internal defect is present.

The aim of the present invention is to provide ail apparatus and method which allows a fault to be detected using magnetic flux monitoring and furthermore, allow the accurate identification of whether the fault is positioned on the external surface of the pipeline or internal surface of the pipeline and to do so without the need for visual checking to be relied on.

In a first aspect of the invention there is provided apparatus for the analysis of a pipeline condition, said apparatus mountable on the external surface of the pipeline and including a means for inducing a magnetic flux into and at least partially through the wall of the pipeline adjacent the location of the apparatus and a means for monitoring the magnetic flux level and characterised in that there is provided a sensing means at the external surface of the pipeline for detecting a change in condition of the material of the pipeline.

In one embodiment, the apparatus is provided to be moved around and/or along a length of pipeline with changes in the magnetic flux and the sensing means being monitored.

In one embodiment, the sensing means is a proximity sensor which is used to determine a change in condition of or near to the external surface of the pipeline.

In one embodiment, the apparatus is particularly useful in relation to a cast iron material pipeline, wherein the proximity sensor changes in response to a change in the material structure and so allows the determination of a change in condition of the cast iron to be identified and located so as to indicate, for example, the formation of graphite the external surface of the pipeline. The location of the graphite would not be identifiable by a visual check of the cast iron pipe, in accordance with conventional methods.

In one embodiment, the apparatus includes a jacket which is locatable around the circumference of the pipeline and, at spaced locations around the jacket, are located magnetic flux monitoring means and proximity sensors.

In an alternative arrangement, particularly for pipes of larger diameter, the apparatus is mounted on a track, with the track, in turn, being mounted along a section of the pipeline, said apparatus moving along the track and the track and apparatus subsequently positioned at other locations around the circumference of the length of pipeline.

In one embodiment, the sensing means used for magnetic flux detection is a Hall effect sensor.

In a further aspect of the invention there is provided a method for the analysis and detection of changes in condition of a pipeline, said method comprising the steps of moving apparatus containing a magnetic flux inductor and detection means and a proximity sensor along and/or around a portion of pipeline, monitoring the readings from the magnetic flux detector and the proximity sensor, identifying changes in the magnetic flux and/or proximity sensor and characterised in that, a change in condition of both the magnetic flux and proximity sensor indicates the existence of a change in condition of or near to the external surface of the pipeline and a change in condition in the magnetic flux but not in the proximity sensor indicates a change in condition located on or near to the interior surface of the pipeline.

As the proximity sensor is used to monitor the change in condition of the external pipeline so changes in the material. Structure on or near the external surface can be differentiated from changes in condition on the internal surface of the pipeline and hence an accurate indication of the location of the change in condition of the pipeline material is provided. Furthermore, the extent of change in the proximity sensor and also extent of change of magnetic flux can be used to determine the size and depth of the change in condition.

In one embodiment, the pipeline is made from cast iron and the proximity sensor indicates the existence of areas of graphite rather than cast iron material on or near the external surface of the pipeline which would not otherwise be detectable.

In one embodiment, the method includes the steps of removing a section of pipeline as a sample, performing the method on the same as indicated herein and then using the results of the condition of the pipeline sample to represent the condition of a length of the pipeline from which the sample was removed. In one embodiment, a one meter long sample of pipeline is used to reach a conclusion as to the condition of 1,000 metres of pipeline. This has been adopted by many of the U.K Water Companies.

Over time, the method includes the step of building a history of faults and defects which are represented by particular detected magnetic flux changes and/or proximity sensor changes and, in the subsequent analysis of new samples of pipeline, reference is made to the historic data to teach a conclusion as to the type and effect of the change in condition represented by detected readings.

A specific embodiment of the invention is now described with reference to the accompanying drawings, wherein.

Figure 2:
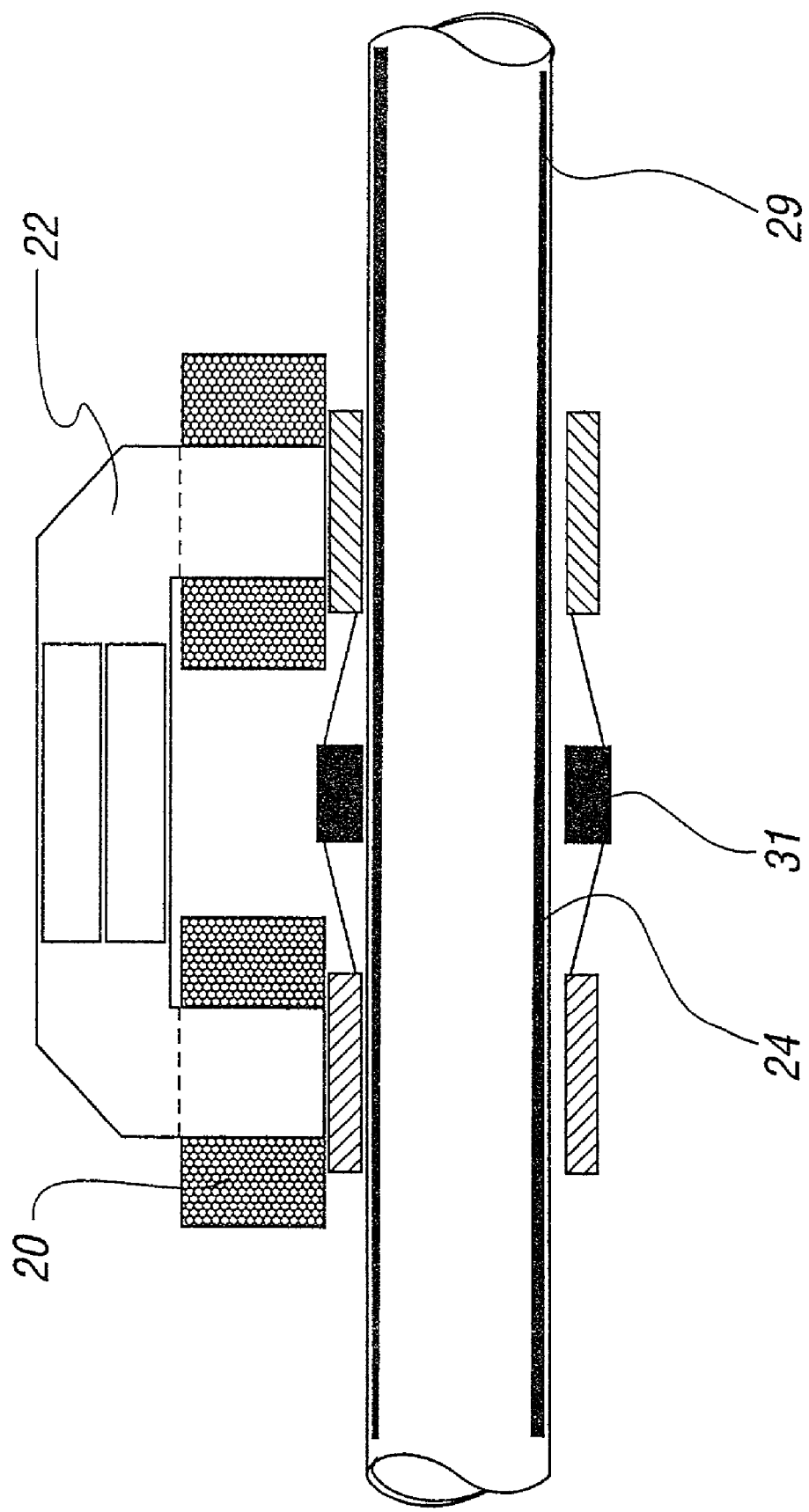
FIG. 2 illustrates one embodiment of the invention in schematic manner.
Figure 3A:
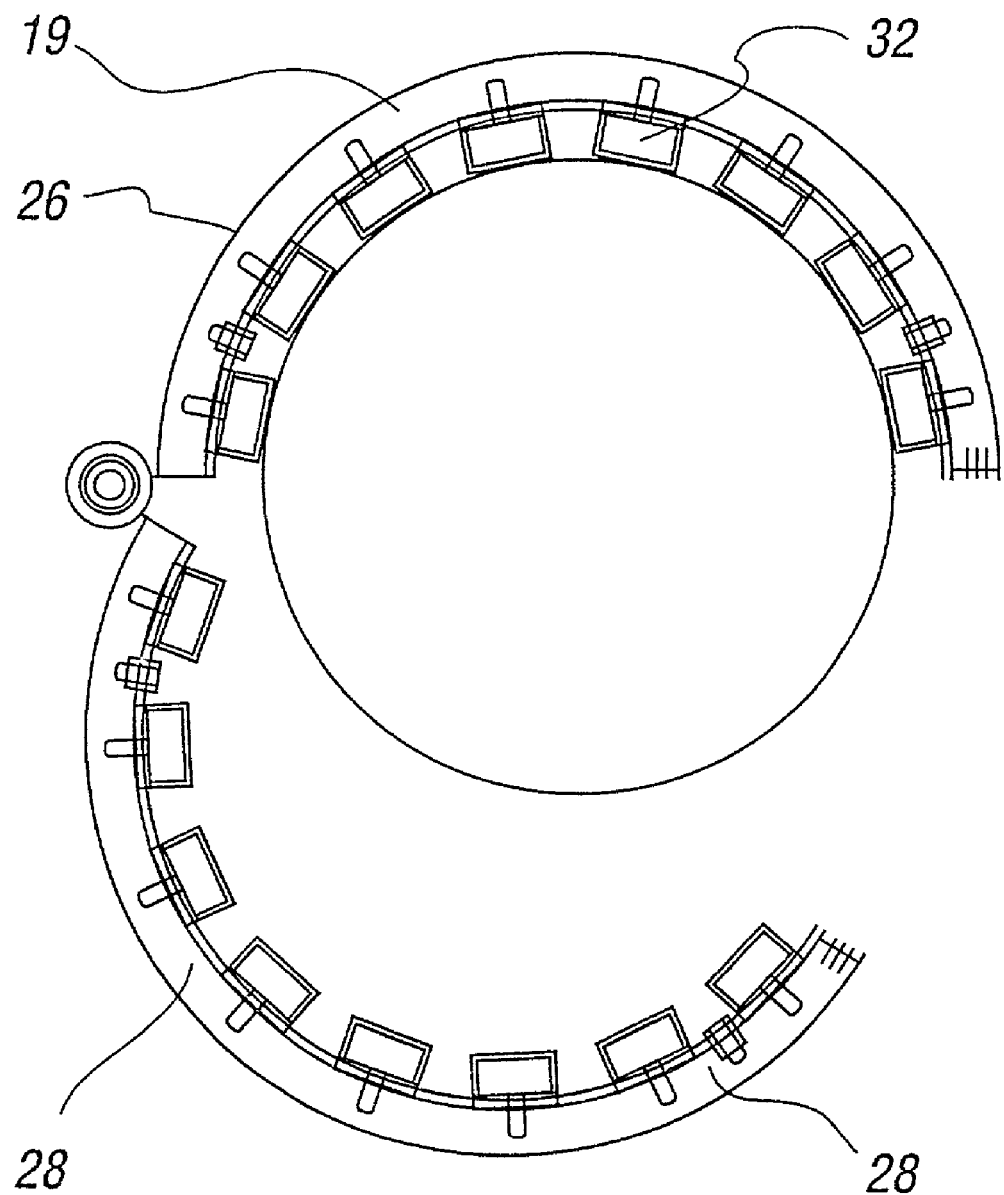
Figure 3B:
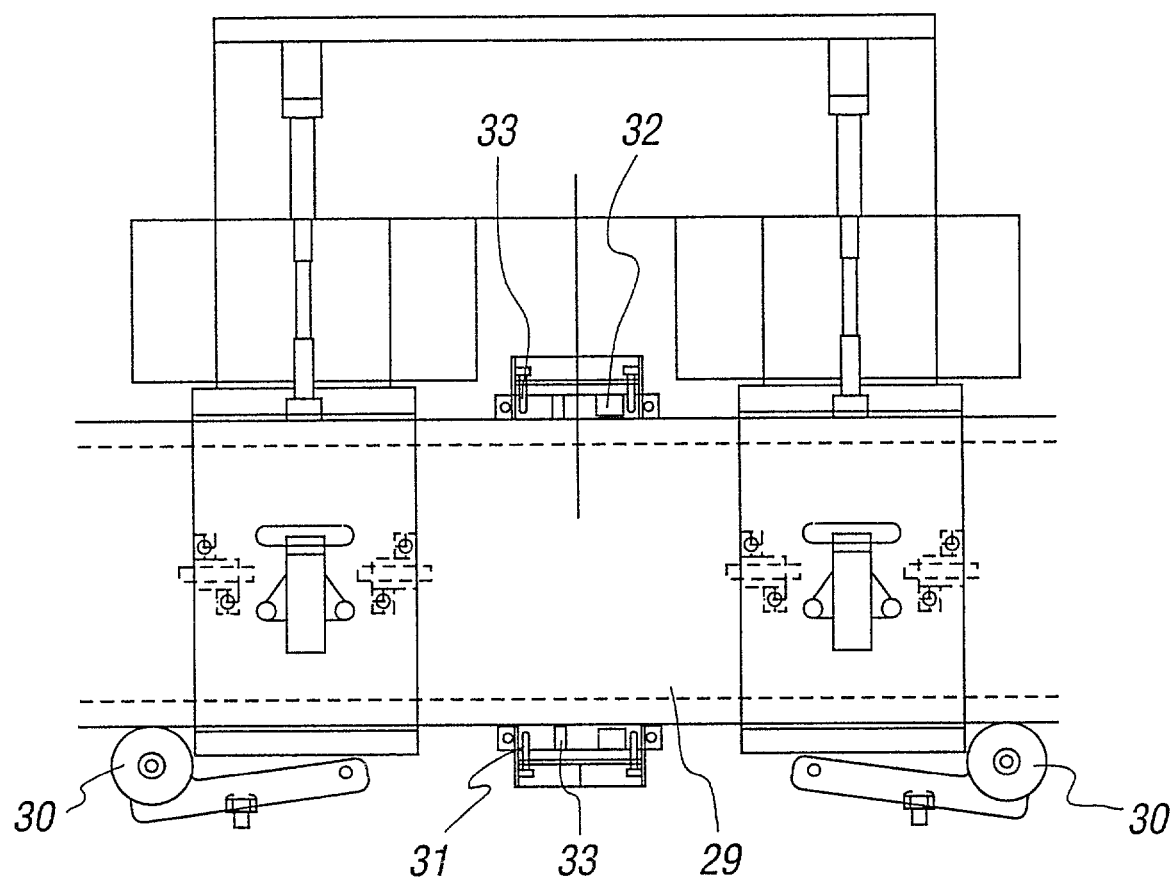
Figure 3C:
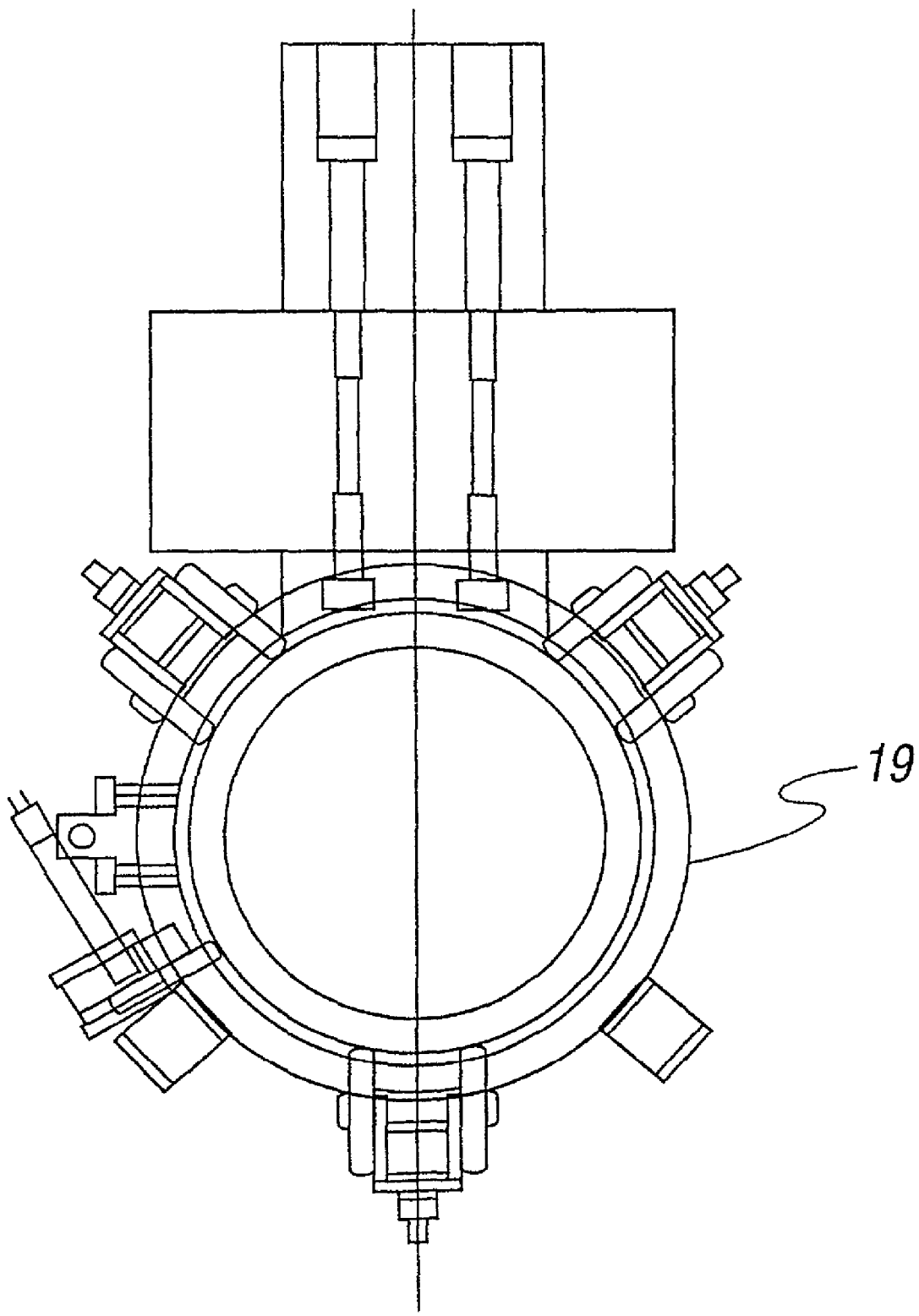
Figure 3D:
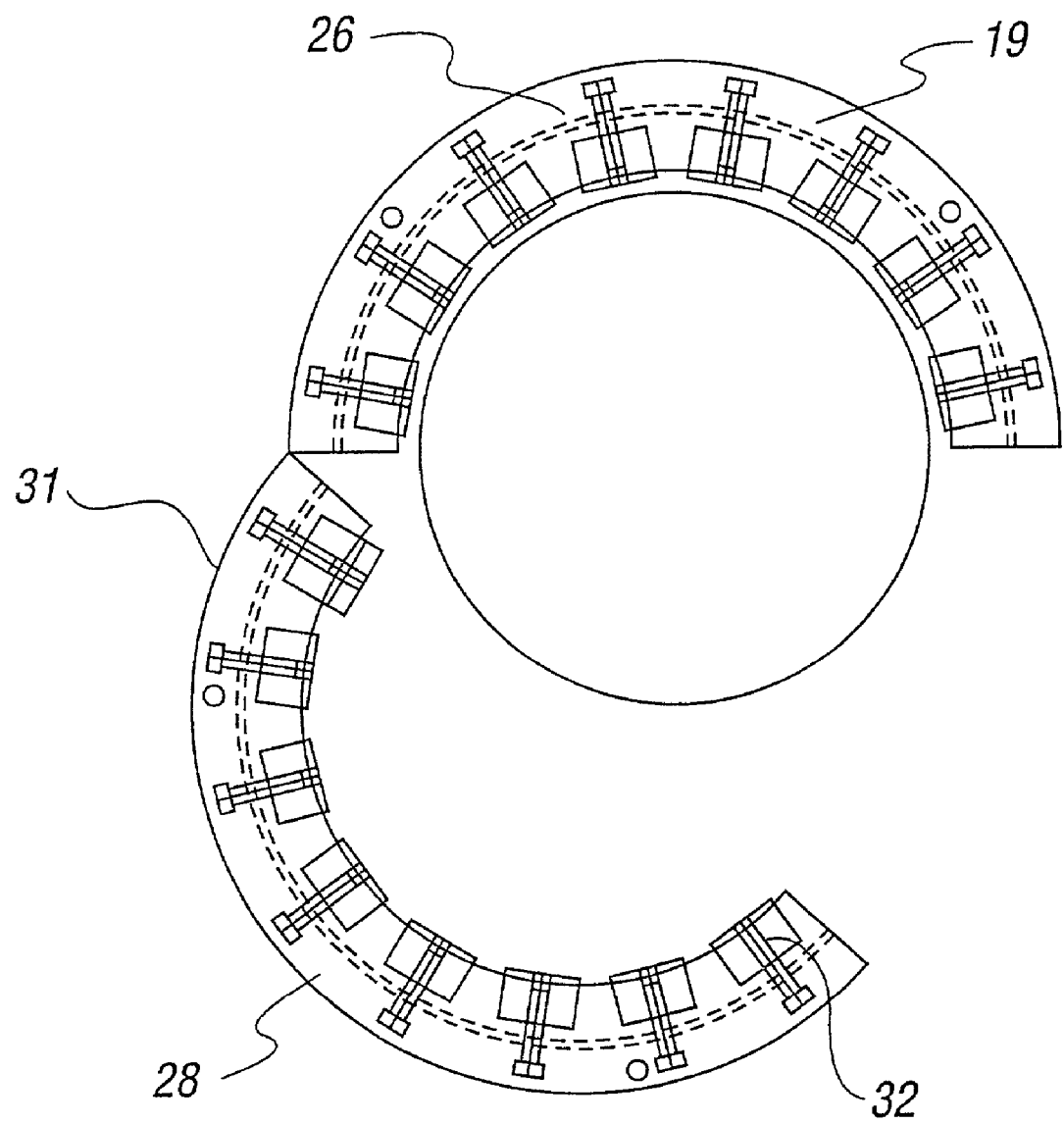
Figure 3E:
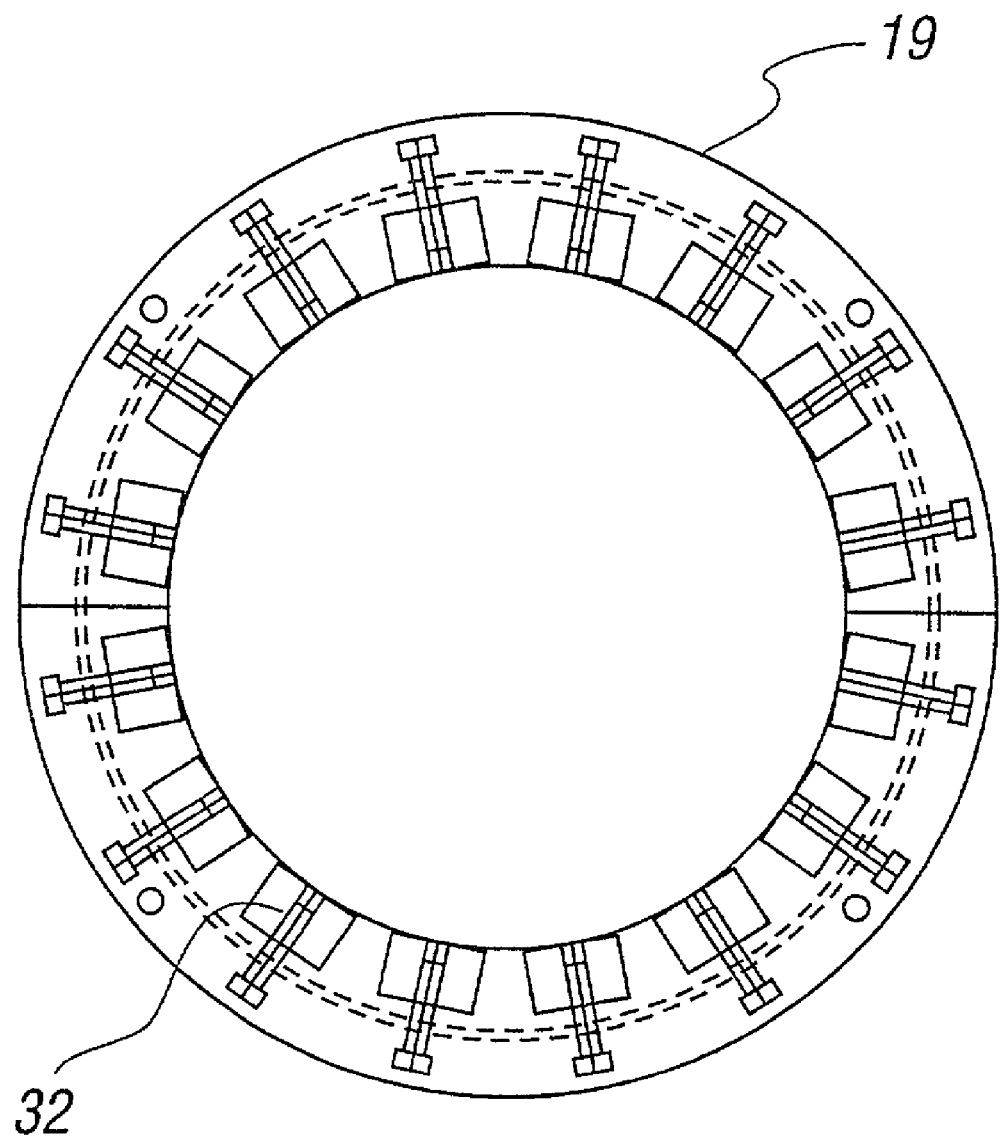
Figure 4A:
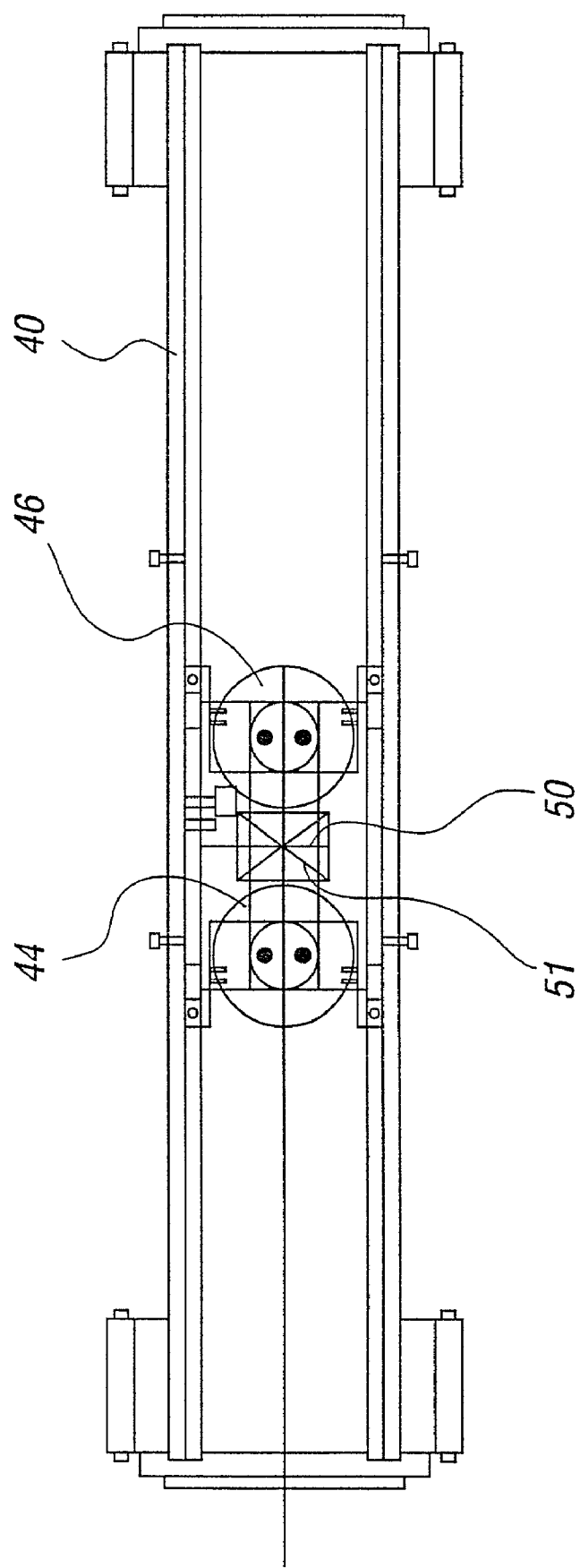
Figure 4B:
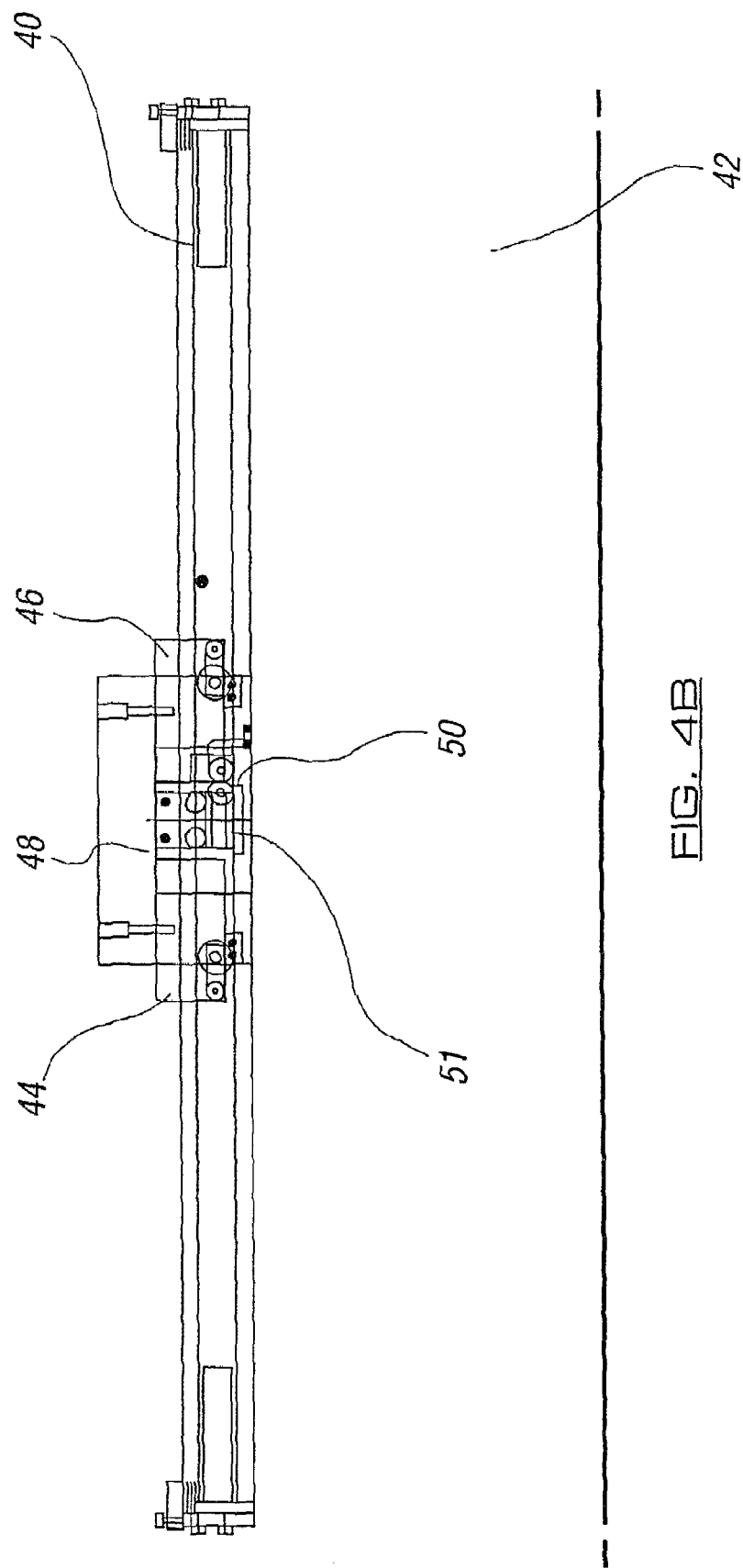
Figure 4C:
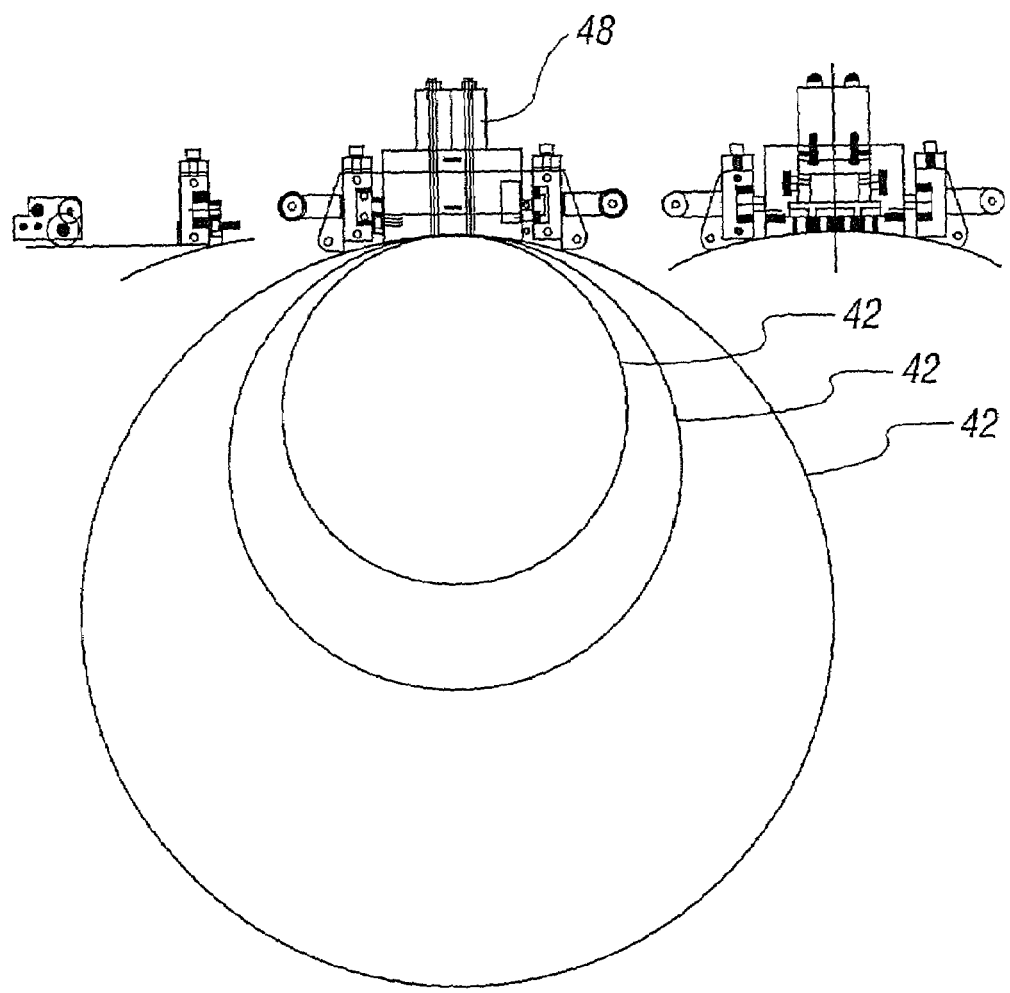
Figure 4D:
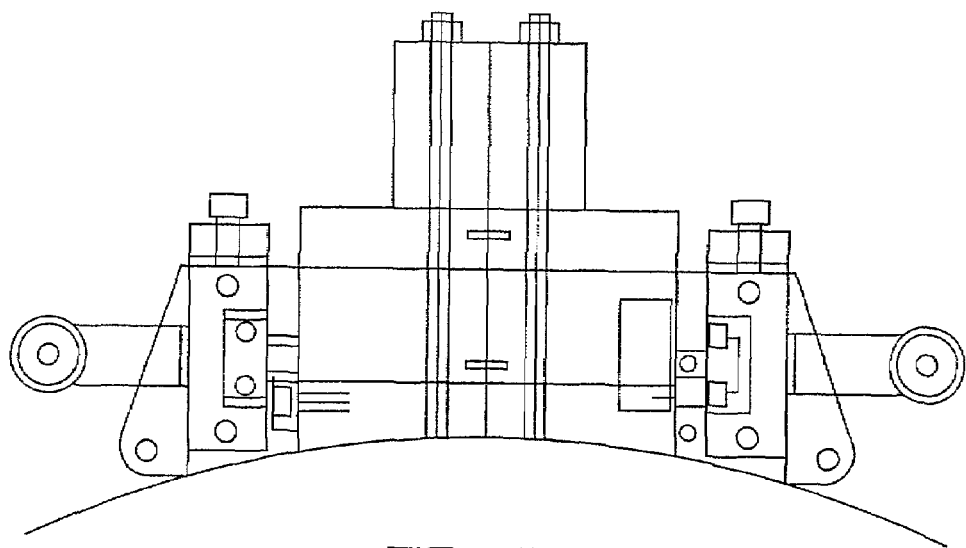
Figure 4E:
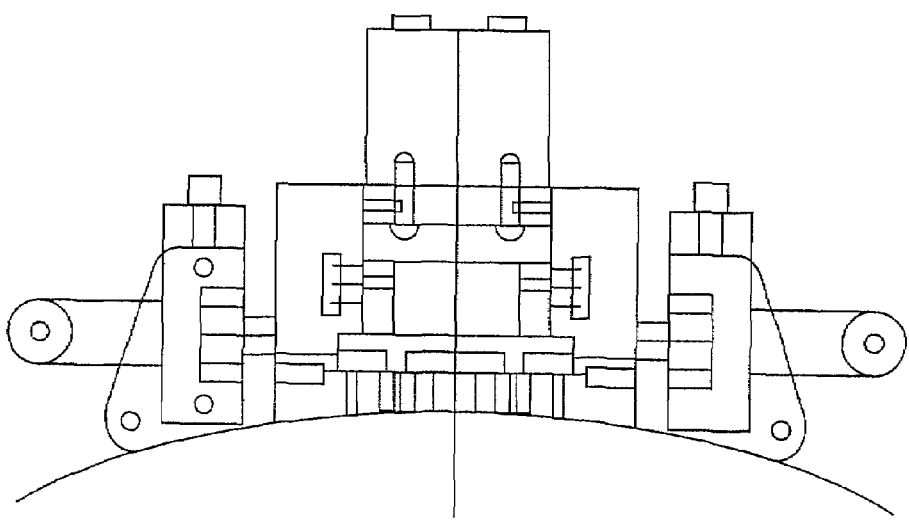
Figure 4F:
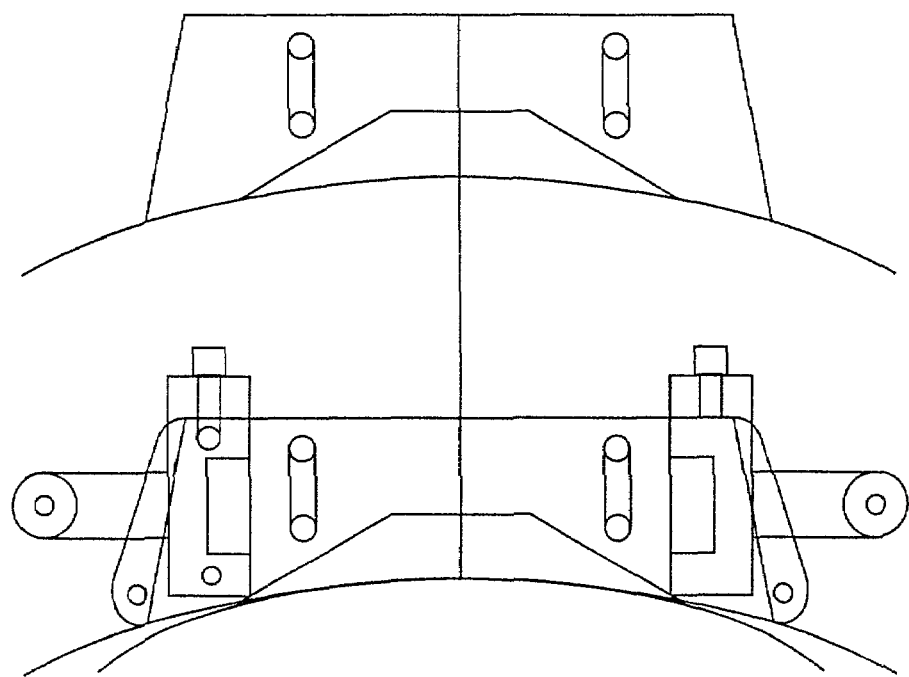
Figure 4G:
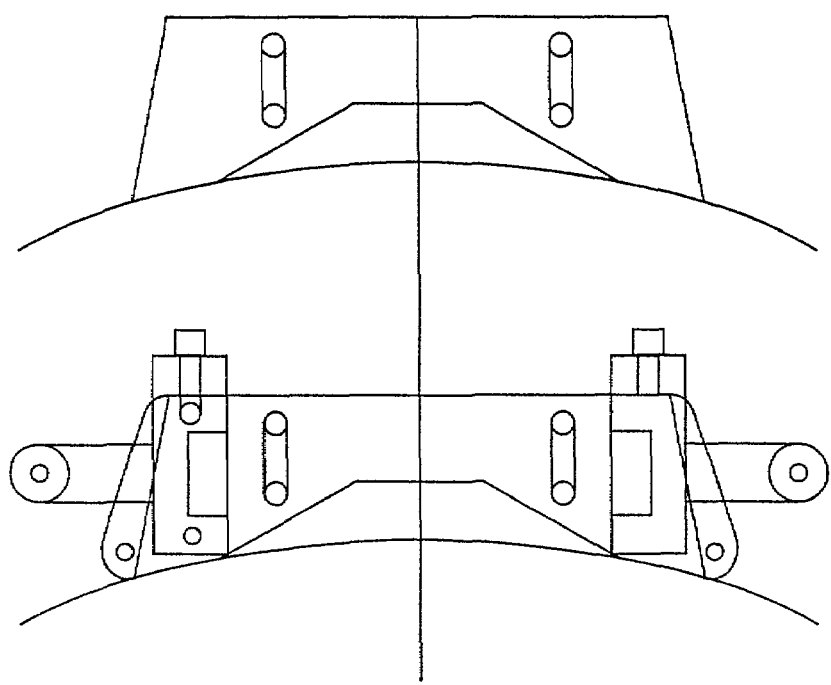
Figure 4H:
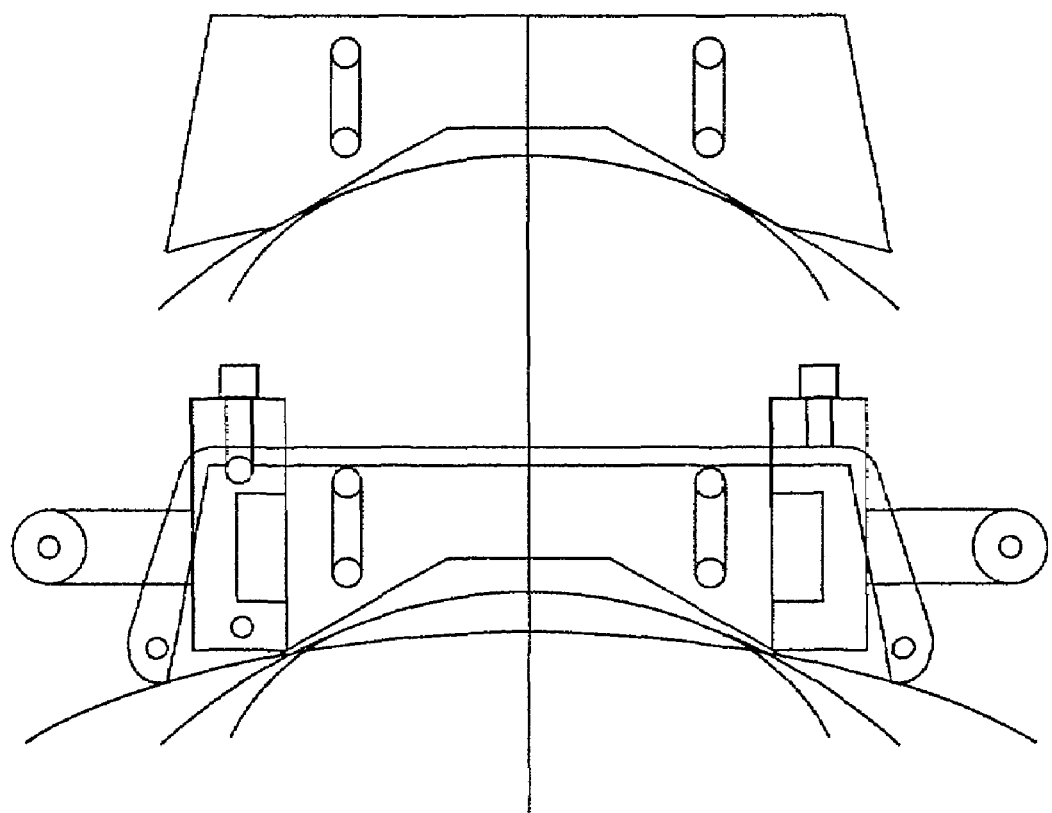

FIGS. 3A–E illustrate in mote detail, the schematic apparatus shown in FIG. 2; and FIGS. 4A–H illustrate a further embodiment of the invention.

Figure 1:
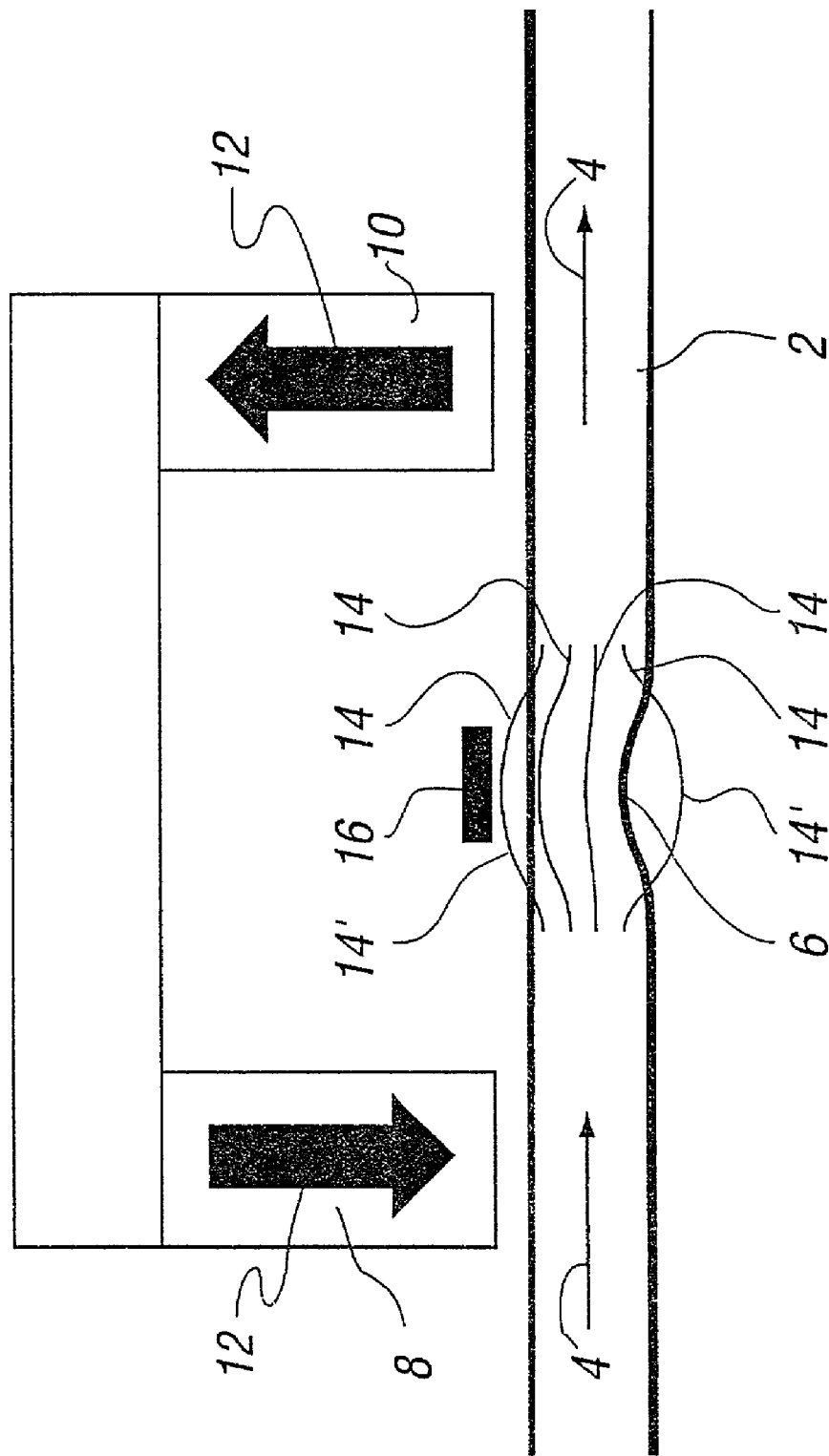
FIG. 1 illustrates the conventional provision of magnetic flux leakage along a pipeline.

Referring firstly to FIG. 1, which is a schematic representation of the invention, there is shown the manner in which magnetic flux can be generated in a pipeline 2 along which a liquid is moving as indicated by arrows 4. In this case, on the interior wall of the pipeline there is a protrusion 6 which may be caused by, for example, corrosion. The magnetic flux is induced by the conductor apparatus 8 and 10 which causes generation and movement of the magnetic flux as indicated by the arrows 12 and through the pipeline as indicated by the lines 14. When the interior and exterior surfaces of the pipeline are smooth, and generally fault free the lines 14 will be generally parallel but the provision of the protrusion 6, causes leakage of magnetic flux through the pipeline walls as indicated by the lines 14'. The change in magnetic flux is monitored by the monitoring means 16.

FIGS. 2 and 3 illustrate one embodiment of the invention which incorporates this feature of FIG. 1 and which also incorporates additional features which render the same inventive.

The example of the apparatus now described has been designed to inspect pipe work in the pipeline size range 3" to 6" diameter constructed from any of the materials of cast iron, ductile iron, spun iron and steel.

In this version of the inspection tool, a jacket 19 is provided to fit around the pipeline and the magnetic flux flow circuit is designed to allow the electromagnets 20, 22 at each end of the apparatus detector array to induce magnetic flux into the pipe section around the full circumference of the pipe. Similarly, the flux leakage detection element 31 of the system is arranged to sense leakage at a number of selected predetermined radial positions at points around the pipe circumference.

The elements of the detector array, jacket, magnetic flux induction and magnetic flux leakage, have been designed to allow the jacket 19 to split in half to two hinged parts 26, 28 to facilitate assembly onto and removal from the pipe.

The apparatus is fitted with wheels 30 and a suspension system that serve to facilitate movement of the apparatus along the pipe section 29 being inspected, and to maintain the required air gap between the pipeline wall and the detector array. This system allows adjustments to be made in order to accommodate variations in pipe geometry.

A sensor ring 31, including the monitoring means in the form of Hall effect sensors 32, are incorporated to detect magnetic flux leakage and located in each or at selected intervals, proximity sensors 33 are also fitted to enable the distinction and location of internal and external defects of the pipeline to be determined as the apparatus moves along the same.

The principal operation of the apparatus is to saturate the pipe with magnetic flux. Resulting from this, there will be a base flux leakage reading due to the saturation, continuously identified by the Hall effect sensor. Where there is a defect present in the metallic wall that effectively reducing wall thickness cross section then while normally magnetic flux would prefer to travel through metal rather than air because its path is restricted, then more flux leaks externally across the defect. The Hall effect sensors detect this change in flux leakage. Hall effect sensors are commercially available and may be purchased from Farnell Electronic Components Limited, Canal Road, Leeds, LS12 2TU, United Kingdom.

The proximity sensor is sensitive to the presence of the pipe material beneath it. When passing along a pipe showing no or insignificant corrosion a constant output signal in terms of volts would be expected to be received from the proximity sensors. However, if a change in condition is detected on or near the external surface of the pipeline the proximity sensor reading will change.

Electric inductive proximity switches are non-contact electronic sensors and recognize the presence of any conducting metal target. The in-built oscillator creates a high frequency electromagnetic field on the pipe surface from which eddy currents are induced, irrespective of wall thickness. Where surface defects are present then there is a change in the eddy current profile. As the name suggests, this sensor has a limited range of typically 2–4 mm from the oscillator and hence only detects changes in eddy currents due to defects on the external surface. Any defects on the internal surface would be well outside the range of the device and would not be detected above the base surface eddy current. The proximity sensors are potted in resin and housed in a plastic block that is structurally attached to the apparatus. Such proximity sensors are commercially available and can be purchased from Farnell Electronic Components Limited, Canal Road, Leeds, LS12 2TU, United Kingdom.

A means (not shown) of recording distance moved by the detector array along the pipe section is also provided.

Another form of the apparatus, required for larger diameter pipes, is shown in FIGS. 4A–H although the magnetic flux generator/leakage detection system, detector array is similar for both detection systems. However, in this embodiment, the apparatus is mounted on a track 40 which facilitates movement along the pipe section 42 under inspection with FIGS. 4C–4H illustrating the apparatus in use on pipelines with different diameters.

The track 40 is strapped to the pipe 42 to allow movement of the detector array along the pipe section to be inspected.

The detector array is moved by pulling it by hand, along the track, thus scanning the pipe section below it.

The track is then moved in stages circumferentially around the pipe, by reducing the clamping action of the strap, to allow another adjacent pipe length to be inspected. This process continues until the entire pipe circumference has been inspected, the clamping straps are then released and the whole assembly can be removed from the pipe.

The magnetic flux generator consists of two electromagnets 44, 46 fixed to a connecting bar 48, which separates them and provides a return magnetic flux path between them. When this assembly is placed on the track above the pipe being inspected the pipe structure provides the final element in the magnetic flux flow path.

The magnetic flux leakage monitor 50 of the detector array 51 is located between the electromagnets and consists of Hall effect sensors fixed into a support frame, which not only accurately position the sensors above the pipe section but also places the sensors in a predetermined radial position. The proximity sensors are also located within the detector array.

The detector array 51 is fitted with a means of recording its position relative to the support track and hence in relation to the pipe section being scanned.

The support track can be fitted with handles on each side to facilitate handling and transport to and from the inspection site.

The apparatus and method, when used with a pipe which has areas of corrosion present, can identify a fault and where, in relation to the pipeline, the fault is located. Considering a cast iron pipeline as an example, this material is characterised in that when corroding, the iron goes into solution leaving behind graphite flakes. Over a period of time the cast iron structure becomes a composite of the original cast iron and a graphite matrix. The graphite flakes not only retain the shape of the original pipe section but also camouflage the roughened pipe subsurface and the true extent of the corrosion is not evident and the original strength of the pipe section is considerably degraded. This corrosion behaviour is also typical of cast or spun iron, ductile iron but not of steel.

By using the apparatus and method of the invention, the proximity sensor can detect the interface between the graphite layer and the original pipe material and register the change by change in voltage as the detector array passes over the corroded area if that area is at or near the external surface of the pipeline. However, the proximity sensor does not react in this way when moving over an area of the pipe with corrosion at or near the internal wall of the pipeline as the proximity sensor is set so as not to detect through the depth of the pipe wall. In this way the detector array can detect and distinguish between external and internal corrosion, as firstly the magnetic flux detection detects corrosion and the proximity sensor reacts if the corrosion is at or near the external surface of the pipeline.

In use the detector array is first assembled onto the pipe section, and then pulled over the section to be inspected and a means of determining the relative position of the detector array on the pipe section is provided.

With both embodiments of apparatus the method of use is such that the severity and position of the effects and the remaining pipe wall thickness can be indicated by changes in flux leakage detected by the Hall effect sensors which in turn are transmitted as a change in voltage to the data processing system and associated software.

In addition to this, the proximity sensors provide an indication of whether the defects ate external or internal.

Software can be used which allows the interpretation of the Hall effect, proximity and detector array positional data in terms of defect size, pipe wall thickness and geometrical orientation of the defects, to allow a report to be provided and, if necessary, a prediction of the life expectancy of the pipework to be provided to allow improved maintenance planning.

What is claimed is:

1. Apparatus for the analysis of a pipeline condition, said apparatus mountable on the external surface of the pipeline and including a means for inducing magnetic flux into and at least partially through the wall of the pipeline adjacent the location of the apparatus and a jacket which is locatable around the circumference of the pipeline, characterised in that magnetic flux monitoring means and proximity sensors are provided at spaced locations around the jacket, said proximity sensors detecting changes in the condition of the pipeline wall material at or near the external surface of the pipeline wall, such that the magnetic flux monitoring means can detect a fault in the pipeline wall and the proximity sensors indicate whether said fault lies to the external surface of the pipeline wall.

2. Apparatus according to claim 1 characterised in that the apparatus is mounted on a track, the track being mounted along a section of the pipeline, said apparatus movable along the track.

3. Apparatus according to claim 2 characterised in that the track and apparatus are positionable at selected locations around the circumference of the pipeline.

4. Apparatus according to claim 1 characterised in that the magnetic flux monitoring means is a Hall effect sensor.

5. Apparatus for the analysis of a pipeline condition, said apparatus mountable on the external surface at the pipeline and including a means for inducing a magnetic flux into and at least partially through the wall of the pipeline adjacent the location of the apparatus, a jacket which is locatable around the circumference of the pipeline, characterized in that magnetic flux monitoring means and proximity sensors are provided at spaced locations around the jacket for detecting a change in condition of the material of the pipeline such that the magnetic flux monitoring means can detect a fault in the pipeline wall and the proximity sensors indicate whether said fault lies to the external surface of the pipeline wall and further characterised in that the apparatus is positioned on a cast iron pipeline with the proximity sensors detecting changes in response to a change in the pipeline material to graphite at or near the external surface of the pipeline.

6. Apparatus according to claim 5 characterised in that the proximity sensors indicate a change in condition of the cast iron to graphite in terms of a variation in a monitored voltage reading.

7. A method for the analysis and detection of changes in condition of a pipeline, said method comprising the steps of moving an apparatus with a jacket which is located around the circumference of the pipeline containing a magnetic flux induction and detection means and a proximity sensor along and/or around a portion of pipeline, monitoring the readings from the magnetic flux detector and the proximity sensor, identifying changes in the magnetic flux detector and/or proximity sensor a change in condition of the magnetic flux in proximity sensor indicates the existence of a change in condition of or near to the external surface of the pipeline and a change in condition in the magnetic flux detector but not in the proximity sensor indicates a change in condition located on or near to the interior surface of the pipeline, and the proximity sensor senses changes in the external surface of the pipeline.

8. A method according to claim 7 characterised in that the proximity sensor is only used to monitor the change in condition of the external pipeline so the same can be differentiated from changes in condition on the internal surface of the pipeline.

9. A method according to claim 8 characterised in that an accurate indication of the location of the change in condition with respect to location on the pipeline and within the pipeline wall is provided.

10. A method according to claim 8 characterised in that the extent of the change measured by the proximity sensor and also extent of change of magnetic flux are used to determine the size and depth of the change in condition.

11. A method according to claim 7 characterised in that the method includes step of compiling a history of faults and defects which are represented by particular magnetic flux changes and/or proximity sensor changes and, in the subsequent analysis of new samples of pipeline, reference is made to the historic data to reach a conclusion as to the type and effect of the change in condition detected.

12. A method for the analysis and detection of changes in condition of a pipeline, said method comprising the steps of moving an apparatus with a jacket which is located around the circumference of the pipeline containing a magnetic flux induction and detection means and a proximity sensor along and/or around a portion of pipeline, monitoring the readings from the magnetic flux detector and the proximity sensor, identifying changes in the magnetic flux detector and/or proximity sensor a change of condition of both the magnetic flux detector and proximity sensor indicates the existence of a change in condition of or near to the external surface of the pipeline and a change in condition in the magnetic flux detector but not in the proximity sensor indicates a change in condition located on or near to the interior surface of the pipeline, additionally characterised in that the proximity sensor senses changes in the external surface of the pipeline, and further characterised in that the method includes the steps of removing a section of pipeline to form a sample, performing the method as and using the results of the condition of the pipeline sample to represent the condition of a length of pipeline from which the sample was removed.

13. A method according to claim 12 characterised in that a one meter long sample of pipeline is used to represent the condition of 1,000 meters of pipeline.

* * * * *